US006187982B1

(12) United States Patent
Beck et al.

(10) Patent No.: US 6,187,982 B1
(45) Date of Patent: Feb. 13, 2001

(54) PROCESS FOR CONVERTING DIENES AND OXYGENATES TO PARA-XYLENE AND LIGHT OLEFINS

(75) Inventors: Jeffrey S. Beck, Burlington; Stephen H. Brown, Princeton; William A. Weber, Marlton, all of NJ (US)

(73) Assignee: Mobil Oil Corporation, Fairfax, VA (US)

( * ) Notice: Under 35 U.S.C. 154(b), the term of this patent shall be extended for 0 days.

(21) Appl. No.: 09/419,228

(22) Filed: Oct. 15, 1999

(51) Int. Cl.[7] .............................. C07C 2/00; C07C 1/00; C07C 1/20; C07C 15/067; C07C 4/06

(52) U.S. Cl. .................... 585/409; 585/319; 585/324; 585/330; 585/639; 585/640; 585/408; 585/407; 585/418; 585/469; 585/648; 208/69; 208/70

(58) Field of Search ................................. 585/314, 324, 585/330, 639, 640, 653, 408, 409, 407, 418, 464, 648; 208/69, 70

(56) References Cited

U.S. PATENT DOCUMENTS

| 4,049,573 | 9/1977 | Kaeding | 252/432 |
|---|---|---|---|
| 4,088,706 | 5/1978 | Kaeding | 260/668 R |
| 4,097,367 | 6/1978 | Haag et al. | 208/135 |
| 4,356,338 | 10/1982 | Young | 585/407 |
| 4,480,145 | 10/1984 | Brennan et al. | 585/640 |
| 4,751,339 | 6/1988 | Beech, Jr. et al. | 585/415 |
| 5,053,579 | 10/1991 | Beech, Jr. et al. | 585/533 |
| 5,110,776 | 5/1992 | Chitnis et al. | 502/64 |
| 5,231,064 | 7/1993 | Absil et al. | 502/68 |

Primary Examiner—Walter D. Griffin
Assistant Examiner—Thuan D. Dang
(74) Attorney, Agent, or Firm—Peter W. Roberts

(57) ABSTRACT

A process useful in steam cracking is disclosed for selectively converting a feed comprising $C_4+$ dienes and oxygenate to a product comprising increased $C_2+$ monoolefins and para-xylene levels by contacting said feed under diolefin conversion conditions with a catalyst comprising a porous crystalline material having a Diffusion Parameter for 2,2-dimethylbutane of about $0.1–100 \text{ sec}^{-1}$ when measured at a temperature of 120° C. and a 2,2-dimethylbutane pressure of 60 torr (8 kPa), a temperature of 430° C. and 0.5 WHSV.

20 Claims, No Drawings

PROCESS FOR CONVERTING DIENES AND OXYGENATES TO PARA-XYLENE AND LIGHT OLEFINS

FIELD OF THE INVENTION

The present invention relates to a process for converting low value dienes, such as those found in pygas streams from steam cracking, to higher value para-dialkylbenzenes, such as p-xylene, and light olefins such as ethylene and propylene.

BACKGROUND OF THE INVENTION

Steam cracking of ethane to form lower olefins such as ethylene and propylene provides undesirable low value dienes (diolefins) in pygas as well. Diolefins are extremely reactive, unstable, and difficult to process in conventional refinery units. For example, the reactive di-olefins can form gum which plugs conventional hydrotreating beds as well as plugging upstream heat exchangers or heaters. Accordingly, refiners have often had to resort to extreme and expensive measures to process these materials, e.g., high pressure hydrotreating. Catalytic diolefin conversion upstream of conventional hydrotreating is also possible, e.g., UOP, Inc.'s Platfining process, which operates at temperatures low enough to prevent gum formation. U.S. Pat. No. 4,097,367 discloses upgrading of pyrolysis gasoline from steam cracking to make ethylene, by passing naphtha over Pd/Zn/ZSM-5 at 900° to 1200° F. High temperature processing of C5+ fraction converted everything boiling in the BTX range to aromatics, yielding a liquid product with essentially no non-aromatic hydrocarbons boiling above 167° F. U.S. Pat. No. 5,053,579 discloses a process for upgrading unstable olefins, naphthas and dienes, such as coker naphthas, by oligomerizing over shape selective zeolite to gasoline and distillate products. U.S. Pat. No. 4,751,339 discloses a process for upgrading diene-containing olefins to aromatic hydrocarbons by contacting a feedstock of liquid pyrolysis gas byproduct under high severity conditions in a fluidized bed of acidic zeolite catalyst particles, e.g., ZSM-5 in the presence of C3+ alkanes. Aromatics yield is increased by recovering and recycling to the reactor C5+ aliphatic hydrocarbons.

U.S. Pat. No. 4,088,706 describes converting methanol to a mixture of $C_2$ to $C_3$ olefins and mononuclear aromatics, particularly p-xylene, by contacting with a shape-selective zeolite having a Constraint Index of 1 to 12 which has been modified by adding oxide of boron or magnesium either alone or in combination or in further combination with oxide of phosphorus. U.S. Pat. Nos. 4,049,573 and 4,088,706 disclose modifying zeolites, such as ZSM-5 with oxides of boron or magnesium, either alone or in combination or in further combination with oxide of phosphorus, increases the yield of p-xylene in the catalytic conversion of methanol to olefins and aromatics. U.S. Pat. No. 4,480,145 discloses increasing ethylene yield in the catalytic conversion of methanol over ZSM-5 by moderating diffusivity of the zeolite by use of large crystal form of the zeolite and by silica "stuffing" of the zeolite pores. U.S. patent application Ser. No. 09/055,478 (Docket No. 10017), filed Apr. 6, 1998, which is a continuation-in-part of U.S patent application Ser. No. 08/725,277, filed Oct. 2, 1996 discloses a catalyst for converting methanol to $C_2$ to $C_4$ olefins having a Diffusion Parameter for 2,2-dimethylbutane of 0.1–20 $sec^{-1}$ such as phosphorus oxide-containing ZSM-5.

None of the prior art processes describe a way to efficiently convert a mixture of oxygenates and unstable diolefins to high value petrochemicals, e.g., ethylene, propylene, benzene, toluene and xylenes.

It would be desirable to provide a way to efficiently convert unstable by-products of steam cracking to higher value hydrocarbons. It would also be desirable to convert unstable diolefin products to higher value aromatic hydrocarbons such as para-dialkylbenzene products such as p-xylene, as well as to the desired lower olefin products of steam cracking. Inasmuch as steam crackers are built to produce ethylene and propylene, a conversion process for diolefins which provides such low molecular weight monoolefins as necessary by-products would be highly efficient for converting diolefins produced during steam cracking. A steam-cracking facility could thus readily increase its capacity for producing ethylene and propylene by employing a method which would simultaneously upgrade pygas dienes to higher value products such as p-xylene, as well as desired incremental ethylene and propylene.

SUMMARY OF THE INVENTION

The present invention relates to a process for selectively converting a feed comprising $C_4$+ dienes and oxygenate to a product comprising increased $C_2$+ monoolefins and para-dialkylbenzene levels which comprises a) contacting said feed under diolefin conversion conditions with a catalyst comprising a porous crystalline material having a Diffusion Parameter for 2,2-dimethylbutane of about 0.1–100 $sec^{-1}$ when measured at a temperature of 120° C. and a 2,2-dimethylbutane pressure of 60 torr (8 kPa);

b) recovering a diolefins-depleted product stream rich in monoolefins and $C_8$+ aromatics, including para-dialkylbenzene; and c) optionally recovering a $C_2$+ monoolefins rich stream from said diolefins depleted product stream to provide a $C_8$+ aromatics rich stream.

In another aspect, the present invention relates to a steam cracking process for converting ethane to $C_2$+ olefins which comprises i) contacting an ethane-containing feed with steam under steam cracking conditions to provide a steam cracked product stream comprising $C_2$+ olefins and $C_4$+ diolefins, ii) recovering ethylene and propylene from said steam cracked product stream to provide a $C_4$+ diolefins rich byproduct stream, iii) contacting said byproduct stream, or boiling fractions thereof enriched in dienes, in the presence of oxygenate under diolefin conversion conditions with a catalyst in the presence of oxygenate under diolefin conversion conditions with a catalyst comprising a porous crystalline material having a Diffusion Parameter for 2,2-dimethylbutane of about 0.1–100 $sec^{-1}$ when measured at a temperature of 120° C. and a 2,2-dimethylbutane pressure of 60 torr (8 kPa).

iv) recovering a diolefins depleted stream rich in $C_2$+ mono-olefins and $C_8$+ aromatics, including para-xylene, and v) separating ethylene and propylene from said diolefins depleted stream to provide a $C_8$+ aromatics stream rich in para-xylene.

DETAILED DESCRIPTION OF THE INVENTION

Catalysts

The present invention utilizes a catalyst for selectively converting low value pygas, and added oxygenates, preferably C1 to C3 oxygenates, e.g., methanol, dimethyl ether, ethanol, and diethethyl ether, to higher value products such as para-xylene, e.g., p-xylene, and $C_2$–$C_4$ olefins, e.g., ethylene and propylene. The catalyst comprises a porous crystalline material having a Diffusion Parameter for 2,2-dimethylbutane of about 0.1–100 $sec^{-1}$, preferably 0.1–40 $sec^{-1}$ and most preferably 3–30 $sec^{-1}$, when measured at a temperature of 120° C. and a 2,2-dimethylbutane pressure of 60 torr (8 kPa).

As used herein, the Diffusion Parameter of a particular porous crystalline material is defined as $D/r^2 \times 10^6$, wherein D is the diffusion coefficient ($cm^2$/sec) and r is the crystal radius (cm). The required diffusion parameters can be derived from sorption measurements provided the assumption is made that the plane sheet model describes the diffusion process. Thus for a given sorbate loading Q, the value $Q/Q_\infty$, where $Q_\infty$ is the equilibrium sorbate loading, is mathematically related to $(Dt/r^2)^{1/2}$ where t is the time (sec) required to reach the sorbate loading Q. Graphical solutions for the plane sheet model are given by J. Crank in "The Mathematics of Diffusion", Oxford University Press, Ely House, London, 1967.

The porous crystalline material employed in the process of the invention is preferably a medium-pore size aluminosilicate zeolite. Medium pore zeolites are generally defined as those having a pore size of about 5 to about 7 Angstroms, such that the zeolite freely sorbs molecules such as n-hexane, 3-methylpentane, benzene and p-xylene. Another common definition for medium pore zeolites involves the Constraint Index test which is described in U.S. Pat. No. 4,016,218, which is incorporated herein by reference. In this case, medium pore zeolites have a Constraint Index of about 1–12, as measured on the zeolite alone without the introduction of modifiers and prior to any treatment to adjust the diffusivity of the catalyst. In addition to the medium-pore size aluminosilicate zeolites, other medium pore acidic metallosilicates, such as silicoaluminophosphates (SAPOs), can be used in the process of the invention.

Particular examples of suitable medium pore zeolites include ZSM-5, ZSM-11, ZSM-12, ZSM-22, ZSM-23, ZSM-35, ZSM-48, and MCM-22, with ZSM-5 and ZSM-11 being particularly preferred.

Zeolite ZSM-5 and the conventional preparation thereof are described in U.S. Pat. No. 3,702,886, the disclosure of which is incorporated herein by reference. Zeolite ZSM-11 and the conventional preparation thereof are described in U.S. Pat. No. 3,709,979, the disclosure of which is incorporated herein by reference. Zeolite ZSM-12 and the conventional preparation thereof are described in U.S. Pat. No. 3,832,449, the disclosure of which is incorporated herein by reference. Zeolite ZSM-23 and the conventional preparation thereof are described in U.S. Pat. No. 4,076,842, the disclosure of which is incorporated herein by reference. Zeolite ZSM-35 and the conventional preparation thereof are described in U.S. Pat. No. 4,016,245, the disclosure of which is incorporated herein by reference. ZSM-48 and the conventional preparation thereof is taught by U.S. Pat. No. 4,375,573, the disclosure of which is incorporated herein by reference. MCM-22 is disclosed in U.S. Pat. Nos. 5,304,698 to Husain; 5,250,277 to Kresge et al.; 5,095,167 to Christensen; and 5,043,503 to Del Rossi et al., the disclosure of which patents are incorporated by reference.

Preferably, the zeolite employed in the process of the invention is ZSM-5 having a silica to alumina molar ratio of at least 250, as measured prior to any treatment of the zeolite to adjust its diffusivity.

The required diffusivity for the catalyst of present catalyst is between 0.1 and 100 $sec^{-1}$ and most typically will be between 3 and 30 $sec^{-1}$. Such a catalyst can be produced by steaming an intermediate pore zeolite as described above so as to effect a controlled reduction in the micropore volume of the catalyst to not less than 50%, and preferably to 50–90%, of that of the unsteamed catalyst. Reduction in micropore volume is derived by measuring the n-hexane adsorption capacity of the catalyst, before and after steaming, at 90° C. and 75 torr n-hexane pressure. Steaming of the porous crystalline material is effected at a temperature of at least about 550° C., and can be conducted effectively by adding the catalyst as make-up to the regenerator of a fluid-bed process unit, or can be conducted prior to addition of the catalyst to the process unit.

To effect the desired controlled reduction in micropore volume and diffusivity, it may be desirable to combine the porous crystalline material, prior to steaming, with a phosphorus modifier. The amount of phosphorus modifier, as measured on an elemental basis, may be between about 0.05 and about 20 wt. %, and preferably is between about 1 and about 10 wt. %, based on the weight of the final catalyst.

Incorporation of the phosphorus modifier into the catalyst used in the invention is conveniently achieved by the methods described in U.S. Pat. Nos. 4,356,338, 5,110,776 and 5,231,064, the entire disclosures of which are incorporated herein by reference. Treatment with phosphorus-containing compounds can readily be accomplished by contacting the porous crystalline material, either alone or in combination with a binder or matrix material, with a solution of an appropriate phosphorus compound, followed by drying and calcining to convert the phosphorus to its oxide form. Contact with the phosphorus-containing compound is generally conducted at a temperature of about 25° C. and about 125° C. for a time between about 15 minutes and about 20 hours. The concentration of the phosphorus in the contact mixture may be between about 0.01 and about 30 wt. %.

Representative phosphorus-containing compounds which may be used include derivatives of groups represented by $PX_3$, $RPX_2$, $R_2PX$, $R_3P$, $X_3PO$, $(XO)_3PO$, $(XO)_3P$, $R_3P=O$, $R_3P=S$, $RPO_2$, $RPS_2$, $RP(O)(OX)_2$, $RP(S)(SX)_2$, $R_2P(O)OX$, $R_2P(S)SX$, $RP(OX)_2$, $RP(SX)_2$, $ROP(OX)_2$, $RSP(SX)_2$, $(RS)_2PSP(SR)_2$, and $(RO)_2POP(OR)_2$, where R is an alkyl or aryl, such as phenyl radical, and X is hydrogen, R, or halide. These compounds include primary, $RPH_2$, secondary, $R_2PH$, and tertiary, $R_3P$, phosphines such as butyl phosphine, the tertiary phosphine oxides, $R_3PO$, such as tributyl phosphine oxide, the tertiary phosphine sulfides, $R_3PS$, the primary, $RP(O)(OX)_2$, and secondary, $R_2P(O)OX$, phosphonic acids such as benzene phosphonic acid, the corresponding sulfur derivatives such as $RP(S)(SX)_2$ and $R_2P(S)SX$, the esters of the phosphonic acids such as dialkyl phosphonate, $(RO)_2P(O)H$, dialkyl alkyl phosphonates, $(RO)_2P(O)R$, and alkyl dialkylphosphinates, $(RO)P(O)R_2$; phosphinous acids, $R_2POX$, such as diethylphosphinous acid, primary, $(RO)P(OX)_2$, secondary, $(RO)_2POX$, and tertiary, $(RO)_3P$, phosphites, and esters thereof such as the monopropyl ester, alkyl dialkylphosphinites, $(RO)PR_2$, and dialkyl alkyphosphinite, $(RO)_2PR$, esters. Corresponding sulfur derivatives may also be employed including $(RS)_2P(S)H$, $(RS)_2P(S)R$, $(RS)P(S)R_2$, $R_2PSX$, $(RS)P(SX)_2$, $(RS)_2PSX$, $(RS)_3P$, $(RS)PR_2$, and $(RS)_2PR$. Examples of phosphite esters include trimethylphosphite, triethylphosphite,diisopropylphosphite, butylphosphite, and pyrophosphites such as tetraethylpyrophosphite. The alkyl groups in the mentioned compounds preferably contain one to four carbon atoms.

Other suitable phosphorus-containing compounds include ammonium hydrogen phosphate, the phosphorus halides such as phosphorus trichloride, bromide, and iodide, alkyl phosphorodichloridites, $(RO)PCl_2$, dialkylphosphorochloridites, $(RO)_2PCl$, dialkylphosphinochloroidites, $R_2PCl$, alkyl alkylphosphonochloridates, $(RO)(R)P(O)Cl$, dialkyl phosphinochloridates, $R_2P(O)Cl$, and $RP(O)Cl_2$. Applicable corresponding sulfur derivatives include $(RS)PCl_2$, $(RS)_2PCl$, $(RS)(R)P(S)Cl$, and $R_2P(S)Cl$.

Particular phosphorus-containing compounds include ammonium phosphate, ammonium dihydrogen phosphate, diammonium hydrogen phosphate, diphenyl phosphine chloride, trimethylphosphite, phosphorus trichloride, phosphoric acid, phenyl phosphine oxychloride, trimethylphosphate, diphenyl phosphinous acid, diphenyl phosphinic acid, diethylchlorothiophosphate, methyl acid phosphate, and other alcohol-$P_2O_5$ reaction products.

After contacting with the phosphorus-containing compound, the porous crystalline material may be dried and calcined to convert the phosphorus to an oxide form. Calcination can be carried out in an inert atmosphere or in the presence of oxygen, for example, in air at a temperature of about 150 to 750° C., preferably about 300 to 500° C., for at least 1 hour, preferably 3–5 hours.

The porous crystalline material employed in the process of the invention may be combined with a variety of binder or matrix materials resistant to the temperatures and other conditions employed in the process. Such materials include active and inactive materials such as clays, silica and/or metal oxides such as alumina. The latter may be either naturally occurring or in the form of gelatinous precipitates or gels including mixtures of silica and metal oxides. Use of a material which is active, tends to change the conversion and/or selectivity of the catalyst and hence is generally not preferred. Inactive materials suitably serve as diluents to control the amount of conversion in a given process so that products can be obtained economically and orderly without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with the porous crystalline material include the montmorillonite and kaolin family, which families include the subbentonites, and the kaolins commonly known as Dixie, McNamee, Ga. and Florida clays or others in which the main mineral constituent is halloysite, kaolinite, dickite, nacrite, or anauxite. Such clays can be used in the raw state as originally mined or initially subjected to calcination, acid treatment or chemical modification.

In addition to the foregoing materials, the porous crystalline material can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

The relative proportions of porous crystalline material and inorganic oxide matrix vary widely, with the content of the former ranging from about 1 to about 90% by weight and more usually, particularly when the composite is prepared in the form of beads, in the range of about 2 to about 80 wt. % of the composite.

Preferably, the binder material comprises silica or a kaolin clay.

Procedures for preparing silica-bound zeolites, such as ZSM-5, are described in U.S. Pat. Nos. 4,582,815; 5,053,374; and 5,182,242. A particular procedure for binding ZSM-5 with a silica binder involves an extrusion process.

The porous crystalline material may be combined with a binder in the form of a fluidized bed catalyst. This fluidized bed catalyst may comprise clay in the binder thereof, and may be formed by a spray-drying process to form catalyst particles having a particle size of 20–200 microns.

The catalyst employed of the invention has a very low acid activity. Using the alpha test of acid activity disclosed in *Journal of Catalysis*, volume 61, page 395 (1980), the catalyst of the invention has an alpha value less than 10, preferably less than 5 and typically below 3 making the alpha test an unreliable indicia of the catalyst's performance.

The catalyst of the present invention may be characterized by a hydrothermal stability such that, after steaming at 1025° C. for 45 minutes in 1 atmosphere steam, the catalyst exhibits a methanol conversion activity of at least 50% when contacted with methanol at a methanol partial pressure of 1 atmosphere, a temperature of 430° C. and 0.5 WHSV.

Process Conditions

The process of the invention is preferably carried out in a moving or fluid catalyst bed with continuous oxidative regeneration. The extent of coke loading can then be continuously controlled by varying the severity and/or the frequency of regeneration.

The process of the present invention is conducted at a temperature of at least 300° C., preferably between about 400 and about 650° C., most preferably between about 400 and about 580° C., a hydrocarbon+oxygenate partial pressure of between 0.1 and 10 atm, and a weight hourly space velocity of between 1 and 100.

The feed to the process comprises oxygenates, preferably $C_1$ to $C_3$ oxygenates, e.g., methanol, dimethyl ether, ethanol, diethylether or a mixture of methanol and dimethyl ether in combination with other feed components noted below. The process may be conducted in the presence of added hydrogen, nitrogen, and/or added water such that the mole fraction of hydrogen, nitrogen and/or water in the feed is between 0 and about 99%, preferably <90%.

$C_4+$ dienes suitable for processing by the present invention include those found in pygas, a byproduct of steam cracking. Such dienes include cyclopentadiene, butadienes, pentadienes, hexadienes and methylcyclopentadienes. The molar ratio of $C_4+$ dienes to oxygenate, e.g., methanol, in the feed can be between 0.001 and 1, preferably between 0.01 and 0.5

The feed can also contain aromatics of the type found in pygas such as benzene, toluene, and xylenes. The molar ratio of aromatics, e.g., toluene to oxygenate in the feed can be between 0 and 2. The preferred hydrocarbon feedstock is the entire C4+ stream derived from steam cracking, or a distilled fraction thereof. Preferred fractions are those boiling between isobutane and benzene, between isobutane and isopentane, and between isopentane and benzene. These streams contain numerous olefins, napthenes and paraffins in addition to aromatics and dienes.

The feed can contain at least 50 wt. % water, 15 to 40 wt. % $C_1$ to $C_3$ oxygenate, 0.1 to 10 wt. % dienes, and 0 to 10 wt. % aromatics. In one embodiment the feed comprises oxygenates selected from the group consisting of methanol, dimethylether, ethanol and dimethylether, and contains 60 to 85 wt. % water, 20 to 30 wt. % oxygenate, 1 to 5 wt. % dienes and 0 to 5 wt. % aromatics. In a preferred embodiment, the feed comprises pygas and contains at least 70 to 80 wt. % water, 20 to 25 wt. % methanol, 1 to 3 wt. % dienes and 0 to 2 wt. % toluene, said para-dialkylbenzene is p-xylene, and said dienes comprise cyclopentadiene.

The process of the invention converts $C_4$+ dienes, olefins, and oxygenate feed to a light olefin and aromatics product containing stream. Para-dialkylbenzene content of the product stream comprises over 10 wt. % and typically over 25 wt. % of the aromatics component and preferably more than 40 wt. % of the $C_8$+ aromatics component.

The process of the invention is preferably carried out in a fluidized bed reactor. Pygas may be fed interstage into a fluid-bed reactor in multiple stages, e.g., three. This serves to produce a more uniform diene partial pressure throughout the catalyst bed. The dienes are the most reactive feedstock component. Without staged injection, conversion of dienes, the most reactive feedstock component is completed at the bottom of the fluid bed, and the rest of the catalyst bed is not utilized to carry out the desired conversion of dienes. Instead of the most desired reaction with dienes, the methanol in the feed can only react with itself or with olefins.

All of the foregoing U.S. patents are incorporated herein by reference.

The present invention is illustrated by the following examples.

EXAMPLE 1

An experiment was conducted in a downflow fixed-bed unit in which the 18", ½" O.D. quartz reactor with ⅛" O.D. internal quartz thermowell is centered inside a 10", single-zone furnace. Methanol, dicyclopentadiene and aromatic feedstocks (toluene) were obtained from Aldrich Chemical Company, Inc., Milwaukee, Wis. and used as received. Distilled water was produced in-house. Feed was introduced using two high-pressure positive displacement pumps obtained from Isco, Inc., Lincoln, Nebr. Aromatics and methanol were blended in the desired molar ratio and delivered from one pump. The second pump was used to deliver the distilled water. 1/16" O.D. tubing was used to deliver each feedstock to a single, 250-cc vaporizer which was heat-traced and held at 220° C. Vaporized feed flowed from the vaporizer through the reactor, into a 300-cc product back-mixing vessel, through an on-line GC equipped with a 60-m DB Wax column obtained from J&W Scientific Incorporated, Folsom, Calif. and a flame ionization detector (FID), and into a product collection can held at room temperature. Gases produced flowed through the product collection can and finally through a wet test meter. All feed and product lines upstream of the GC sampling were held above 200° C. using heat tracing. On-line total product GC was used to determine product composition.

The diffusion measurements were made on a TA Instruments 2950 Thermalgravimetric Analyzer equipped with a Thermal Analysis 2000 controller, a gas switching accessory and an automatic sample changer. Diffusion measurements were made at 120° C. and 60 torr 2,2-dimethylbutane and data were plotted as uptake versus square root of time. Fixed bed catalytic testing was conducted using a ⅜" (1 cm) outside diameter, down-flow reactor equipped with a thermocouple. Methanol and water were all pumped to the reactor by way of a vaporizer equipped with a static mixer to thoroughly gasify and mix the feedstocks upstream of the reactor. The total reactor effluent was analyzed, on line, by gas chromatography. Methanol conversion was calculated based on hydrocarbon formation only. Selectivities to hydrocarbon product were calculated on a "water free" basis.

The catalyst employed was prepared by the following procedure:

Phosphoric acid, kaolin clay, and 450:1 $SiO_2/Al_2O_3$ ZSM-5 were slurried in water and spray dried to make a typical fluid-bed catalyst. The catalyst was calcined in air at 510° C. The finished catalyst contained 40 wt % ZSM-5 and 4.5 wt % phosphorus. This material had an n-hexane sorption of 33.5, a diffusion parameter of 27, and an alpha of about 7.

The catalyst was steamed at 1 atmosphere and 1050° C. for 45 minutes and the resulting material had an n-hexane sorption of 31 mg/g, an alpha of about 1, and a diffusion parameter ($D/r^2$) of 0.5.

This catalyst was used to convert a feedstock comprising 75 wt. % water, 1.25 wt. % dicyclopentadiene (which upon heating converts to cyclopentadiene), 1.25 wt. % toluene and 22.5 wt. % methanol at 430° C. and 1 atm. total pressure.

Dicyclopentadiene conversion was complete at 20% methanol conversion and 10% toluene conversion. 30 wt. % of the hydrocarbon product was p-xylene, 25 wt. % was ethylene, and 22 wt. % was propylene. The remaining products were largely $C_4$+ olefins and $C_8$+ aromatics other than p-xylene.

The results show that cyclopentadiene can be converted to p-xylene with high selectivity by reaction with methanol. Methanol is likewise converted with high selectivity to ethylene, propylene, and p-xylene.

The process can be used to feed about 18 lbs. of methanol and 2 lbs. of cyclopentadiene to make 10 lbs. of hydrocarbon products (3 lbs. p-xylene, 2.5 lbs. ethylene, 2.2 lbs. propylene, and 2.4 lbs. of byproducts). In one embodiment, cyclopentadienes can be fed interstage into a fluid-bed reactor in three stages allowing high single-pass conversions of both methanol and cyclopentadiene, the latter being substituted for pygas. Pygas contains additional other dienes as well as aromatics (simulated by the addition of toluene to the feed) which can be upgraded to p-xylene with high selectivity.

EXAMPLE 2

A commercially available FCC additive 26:1 ($SiO_2:Al_2O_3$) ZSM-5 catalyst (about 3 wt % P) that had been steamed at 1450° F. for 4 h, comprised of 25 wt % ZSM-5 having an alpha of about 3, a diffusion parameter of 26, and a n-hexane sorption of 25 mg/g, was used to convert a mixture of 90 wt % methanol 5 wt % dicyclopentadiene (converts to 5 wt % cyclopentadiene in the vaporizer) and 5 wt % toluene. The reaction was conducted at atmospheric pressure and 485° C. Dicyclopentadiene conversion was complete at 30% methanol conversion and 10% toluene conversion. 20 wt. % of the hydrocarbon product were xylenes (80% of the xylenes were p-xylene), 20 wt. % was ethylene, and 20 wt. % was propylene. The remaining 40 wt % were largely $C_4$+ olefins and $C_8$+ aromatics other than p-xylene.

It is claimed:

1. A process for selectively converting a feed comprising $C_4+$ dienes and oxygenate to a product comprising increased $C_2+$ monoolefins and para-xylene levels which comprises
   a) contacting said feed under diolefin conversion conditions with a catalyst comprising a porous crystalline material having a Diffusion Parameter for 2,2-dimethylbutane of about 0.1–100 sec$^{-1}$ when measured at a temperature of 120° C. and a 2,2-dimethylbutane pressure of 60 torr,
   b) recovering a diolefins-depleted product stream rich in monoolefins and $C_7+$ aromatics, including para-xylene; and
   c) optionally recovering a $C_2+$ monoolefins rich stream from said diolefins depleted product stream to provide a $C_7+$ aromatics rich stream.

2. The process of claim 1 wherein said feed comprises any combination of methanol, C4+ steam cracker product, and water.

3. The process of claim 1 wherein said feed comprises any combination of methanol, fraction C4+ steam cracker product boiling largely between isobutane and benzene, and water.

4. The process of claim 1 wherein said feed comprises any combination of methanol, fraction C4+ steam cracker product boiling largely between isopentane and benzene, and water.

5. The process of claim 1 wherein said feed comprises any combination of methanol, fraction C4+ steam cracker product boiling largely between isobutane and isopentane, and water.

6. The process of claim 1 wherein said porous crystalline material contains an oxide of phosphorus and has a Diffusion Parameter of about 0.2–100 sec$^{-1}$ and an alpha value less than 10.

7. The process of claim 1 wherein said porous crystalline material contains about 0.05 to about 20 wt. % of an oxide of phosphorus on an elemental basis.

8. The process of claim 1, wherein said porous crystalline material is an aluminosilicate zeolite.

9. The process of claim 8, wherein said zeolite is selected from the group consisting of ZSM-5 and ZSM-11 and has an alpha value less than 5.

10. The process of claim 1, wherein the contacting is effected at a temperature between about 400 and about 650° C., a pressure between about 1–10 atmospheres, and a weight hourly space velocity between about 1 and 10.

11. The process of claim 1, wherein said contacting is carried out in a fluidized bed reactor.

12. A steam cracking process for converting ethane to $C_2+$ olefins which comprises
    i) contacting an ethane-containing feed with steam under steam cracking conditions to provide a steam cracked product stream comprising $C_2+$ olefins and $C_4+$ diolefins,
    ii) recovering ethylene and propylene from said steam cracked product stream to provide a $C_4+$ diolefins rich byproduct stream,
    iii) contacting said byproduct stream, or boiling fractions thereof enriched in dienes, in the presence of oxygenate under diolefin conversion conditions with a catalyst comprising a porous crystalline material having a Diffusion Parameter for 2,2-dimethylbutane of about 0.1–100 sec$^{-1}$ when measured at a temperature of 120° C. and a 2,2-dimethylbutane pressure of 60 torr,
    iv) recovering a diolefins depleted stream rich in $C_2+$ mono-olefins and $C_8+$ aromatics, including para-xylene,
    v) separating ethylene and propylene and aromatics from said diolefins depleted stream.

13. The process of claim 12 wherein said byproducts stream contains at least 50 wt. % water, 15 to 40 wt. % $C_1$ to $C_3$ oxygenate, 0.1 to 10 wt. % dienes, and 0 to 10 wt. % aromatics, and said diolefin conversion conditions comprise temperatures of at least 300° C.

14. The process of claim 12 wherein said byproducts stream comprises oxygenates selected from the group consisting of methanol, dimethylether, ethanol and dimethylether, and contains 60 to 85 wt. % water, 20 to 30 wt. % oxygenate, 1 to 5 wt. % dienes and 0 to 5 wt. % aromatics.

15. The process of claim 12 wherein said byproducts stream contains at least 70 to 80 wt. % water, 20 to 25 wt. % methanol, 1 to 3 wt. % dienes and 0 to 2 wt. % toluene, and said steam cracked product stream comprises pygas.

16. The process of claim 12 wherein said porous crystalline material contains an oxide of phosphorus and has a Diffusion Parameter of about 0.2–5 sec$^{-1}$ and an alpha value less than 5.

17. The process of claim 12 wherein said porous crystalline material contains about 0.05 to about 20 wt. % of an oxide of phosphorus on an elemental basis.

18. The process of claim 12, wherein said porous crystalline material is an aluminosilicate zeolite.

19. The process of claim 18, wherein said zeolite is selected from the group consisting of ZSM-5 and ZSM-11 and has an alpha value less than 1.

20. The process of claim 12, wherein the contacting of said $C_4+$ diolefins rich byproduct stream is effected at a temperature between about 400 and about 650° C., a pressure between about 1–10 atmospheres, and a weight hourly space velocity between about 0.1 and 10, in a fluidized bed reactor.

* * * * *